United States Patent [19]
Bujalski et al.

[11] Patent Number: 5,262,553
[45] Date of Patent: Nov. 16, 1993

[54] METHOD OF CROSSLINKING POLYSILAZANE POLYMERS

[75] Inventors: Duane R. Bujalski, Bay City; Gregg A. Zank; Thomas D. Barnard, both of Midland, all of Mich.

[73] Assignee: Dow Corning Corporation, Midland, Mich.

[21] Appl. No.: 1,986

[22] Filed: Jan. 8, 1993

[51] Int. Cl.⁵ .............................. C07F 5/02; C07F 7/10
[52] U.S. Cl. .................................. 556/402; 528/5
[58] Field of Search ...................................... 556/402

[56] References Cited

U.S. PATENT DOCUMENTS

| | | | |
|---|---|---|---|
| 4,767,728 | 8/1988 | Riccitiello et al. | 556/402 X |
| 4,910,173 | 3/1990 | Niebylski | 501/92 |
| 5,030,744 | 7/1991 | Funayama | 556/402 |
| 5,086,126 | 2/1992 | Mahone | 525/474 |
| 5,118,774 | 6/1992 | Mignani et al. | 556/402 X |
| 5,162,558 | 11/1992 | Ardaud et al. | 556/402 |
| 5,169,908 | 12/1992 | Zank | 525/474 |

OTHER PUBLICATIONS

Seyferth et al., J Am Ceram Soc 73, 2131–2133 (1990).
Noth, Z. Naturforsch, B Anorg Chem, Org. Chem., 16 [9] 618–620 (1961).

*Primary Examiner*—Paul F. Shaver
*Attorney, Agent, or Firm*—Roger E. Gobrogge

[57] ABSTRACT

The present invention describes a novel method for crosslinking polysilazane polymers having Si—H or N—H bonds. The method comprises mixing the polysilazane with a silazane crosslinker having at least 2 boron functional groups which can react with the Si—H or N—H bonds of the polysilazane and then facilitating crosslinking.

5 Claims, No Drawings

METHOD OF CROSSLINKING POLYSILAZANE POLYMERS

BACKGROUND OF THE INVENTION

The present invention relates to a method of crosslinking polysilazane polymers in which boron modified silazanes are used as crosslinkers. The invention also relates to a novel crosslinker comprising boron modified tris(trimethylsilylamino)silane and a method for it manufacture.

A variety of polysilazane oligomers, cyclics, resins and linear polymers are known in the art. Such polysilazanes are characterized as having backbones with alternating silicon and nitrogen atoms. These polymers have found broad utility as precursors to a variety of ceramic materials such as ceramic monoliths, ceramic fibers and matrices for ceramic matrix composites.

To be truly useful as ceramic precursors, however, the polysilazanes must be curable (infusible) to prevent deformation of the ceramic upon heating. Various approaches to providing curability have been suggested. For instance, Mahone in U.S. Pat. No. 5,086,126 discloses a process for adding vinyl groups to a polysilazane such that upon addition of a free radical precursor the polymer would rapidly cure.

Similarly, various references disclose the addition of boron compounds to polysilazanes to provide curability. For instance, Zank in U.S. Pat. No. 5,169,908 discloses the addition of borane to a hydridopolysilazane polymer to render the polymer curable. Funayama et al. in U.S. Pat. No. 5,030,744 discloses the addition of a boron compound to a polysilazane to increase its molecular weight. U.S. Pat. No. 4,910,173 granted to Niebylski discloses the formation of an organoborosilazane by the reaction of a boroxine with a polysilazane. Seyferth et al. in J. Am. Ceram. Soc. 73, 2131-2133 (1990) teaches the reaction of a silazane oligomer with borane to form a higher molecular weight borazine. Finally, Noth in Z. Naturforsch, B. Anorg. Chem. Org. Chem. 16 [9] 618-621 (1961) teaches the reaction of hexamethyldisilazane with diborane to form a higher molecular weight borazine.

As is readily apparent, each of the above references teaches the addition of boron to a polysilazane to render it infusible or to increase the molecular weight of the resultant polymer. By contrast, the present inventors have now discovered that boron-modified silazane crosslinkers can be utilized to render nearly any polysilazane having Si—H or N—H bonds infusible.

SUMMARY OF THE INVENTION

The present invention relates to a method of crosslinking a polysilazane having Si—H or N—H bonds. The method comprises mixing the polysilazane with a silazane crosslinker which has at least 2 boron functional groups that react with the Si—H or N—H bonds. The crosslinking of the mixture may then be facilitated by heating for a time and at a temperature sufficient to crosslink the polysilazane to the desired extent.

The present invention also relates to a novel silazane crosslinker of the structure:

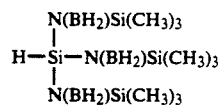

Finally, the invention relates to a method of forming the novel crosslinker which comprises reacting tris(trimethylsilylamino)silane with borane for a time and at a temperature sufficient to form the boron modified silane.

DETAILED DESCRIPTION OF THE INVENTION

The present invention is based on the discovery that a boron modified silazane crosslinker can be used to crosslink polysilazanes and, thus, render them more useful as ceramic precursors. The approach claimed in the present invention allows for better control over the crosslinking reaction and can lower the $T_g$ and storage modulus of the resin to impart a controllable tack depending on the level of crosslinker addition.

The method of curing the polysilazanes of the present invention involves mixing the polysilazane with the crosslinker followed by facilitation of the crosslinking reaction. Upon initiation, the boron of the crosslinker reacts with the Si—H and/or N—H bonds of the polysilazane to form Si—B and/or N—B bonds, respectively, and, thus, cause crosslinking.

The polysilazanes which are useful herein can be any which have N—H or Si—H bonds for reaction. Representative non-limiting examples of such polymers include those of Gaul in U.S. Pat. Nos. 4,312,970, 4,395,460, and 4,340,619, those of Cannady in U.S. Pat. No. 4,540,803, those of Gerdau et al. in European Patent 351,747, those of U.S. Pat. No. 4,543,344, those of European Patent 332,374, those described by Funayama et al. in U.S. Pat. No. 5,030,744 and those of Lebrun et al. in U.S. Pat. Nos. 4,656,300 and 4,689,252, the disclosures of which are all hereby incorporated by reference.

The preferred polymers to be used herein are those of Cannady in U.S. Pat. No. 4,540,803. These polysilazanes are prepared by a method which comprises contacting and reacting in an inert essentially anhydrous atmosphere, trichlorosilane and a disilazane at a temperature in the range of 25° C., to 300° C. while distilling volatile byproducts. The disilazane used in the process has the formula $(R_3Si)_2NH$ where R is selected from the group consisting of vinyl, hydrogen, phenyl and alkyl radicals containing 1 to 3 carbon atoms.

The trichlorosilane is treated with the disilazane in sufficient amounts to react with all of the chlorine in the chlorine containing silane. This is usually an equimolar amount based on the chlorine content of the trichlorosilane.

The disilazane used in the Cannady invention has the formula $(R_3'Si)_2NH$, where R' is vinyl, hydrogen, an alkyl group of 1-3 carbon atoms or a phenyl group. Thus, the R' groups are independently selected from the group consisting of hydrogen, methyl, ethyl, propyl, vinyl and phenyl. Examples of suitable disilazanes include $[(CH_3)_3Si]_2NH$, $[(C_6H_5(CH_3)_2Si]_2NH$, $[(C_6H_5)_2CH_3Si]_2NH$, $[CH_2=CH(CH_3)_2Si]_2NH$, $[CH_2=CH(CH_3)C_6H_5Si]_2NH$, $[CH_2=CH(C_6H_5)_2Si]_2NH$, $[CH_2=CH(C_2H_5)_2Si]_2NH$, $[H(CH_3)_2Si]_2NH$, and $[CH_2=CH(C_6H_5)C_2H_5Si]_2NH$.

An especially preferred embodiment of the Cannady invention involves the reaction of trichlorosilane with hexamethyldisilazane. The resultant polymer produced thereby, hydridopolysilazane, has been shown to have valuable preceramic properties.

The above reactants are brought together in an inert, essentially anhydrous atmosphere. By inert it is meant that the reaction is carried out under a blanket of inert gas such as argon. nitrogen or helium. What is meant by essentially anhydrous is that the reaction is preferably carried out in an absolutely anhydrous atmosphere but minute amounts of moisture can be tolerated.

When the reactants are contacted with each other an intermediate amino compound is formed. It is preferred that the reactants are brought together in such a manner to keep the initial reaction exotherm to a minimum. Upon continued heating additional amino compound is formed and, with further heating, $R_3SiCl$ is distilled from the reaction mixture and the silazane polymer formed. For best results, the rate of heating should be controlled at a rate of less than about 1° C./min. A heating rate of about 0.5° C./min. or less is preferred. As the temperature of reaction is raised, more condensation takes place and crosslinking occurs with residual $R_3Si$ that is not distilled from the mixture acting as a chain stopper. This control allows one to stop the reaction at any point to obtain almost any desired viscosity. The desired temperature range for the reaction is 25° C., to 300° C, with a temperature in the range of 125° C., to 275° C. being more preferred. The length of time that the reaction requires depends on the temperature employed and the viscosity one wishes to achieve.

Although the polymers of the Cannady invention are specifically set forth, nearly any polysilazane with N—H or Si—H bonds may be used in the invention.

The crosslinker used in the present invention is a silazane which has at least 2 boron functional groups. Generally, such silazanes have a low molecular weight, e.g., less than about 1000. Although any such crosslinker would be functional herein, generally they have the structure:

$R_3Si-NR-(SiR_2-NR)_x-SiR_3$

In this structure, R is independently a hydrogen, a hydrocarbon or 1-20 carbon atoms, a hydrocarbon of 1-20 carbon atoms substituted with silicon, nitrogen or boron, or a substituted silicon, nitrogen or boron atom. Specific examples include alkyls such as methyl, ethyl, propyl, butyl, etc, alkenyls such as vinyl, aryls such as phenyl, cycloalkyls such as cyclohexyl, alkaryls, alkylaminos, aminoalkyls, alkylsilyls, silylalkyls, aminosilyls, aminoalkylsilyls, borosilyls, boroaminosilyls, boroalkyls and the like. The above R groups must contain at least 2 boron functional groups per crosslinker molecule. These boron functional groups can be independently selected from the group consisting of hydrogens, halogens, alkoxys, or hydroxys attached to boron. x in the above structure is 0-5.

A preferred crosslinker for use in the present invention has the structure:

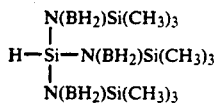

Since each of the B—H bonds of the crosslinker are potential sites for reacting with Si—H or N—H bonds of a polysilazane, the crosslinker is hexafunctional and, thus, can effectively infusibilize the polymer even when used in small amounts.

This crosslinker can be prepared by a number of techniques. Generally for convenience, however, it is formed by reacting tris(trimethylsilylamino)silane with borane to produce the desired crosslinker. Both reactants are known in the art and commercially available. Generally, any source of borane may be used. For instance, borane is available from Aldrich Chemical Co. as complexes with various Lewis bases. These include borane complexes with various amines such as pyridine, butylamine or diethylamine, complexes with sulfides such as methyl sulfide, complexes with phosphines such as triphenylphosphine and complexes with ethers such as tetrahydrofuran. Although any source of borane may be used, the present inventor has found it convenient to use the borane-tetrahydrofuran complex.

The stoichiometric amount of borane used in this reaction is three moles of borane per mole of tris(trimethylsilylamino)silane. It is generally preferred to use two to three moles of borane per mole of tris(trimethylsilylamino)silane. However, greater or lesser amounts may be used. If less than a stoichiometric amount is used, residual N—H will be present. If greater than a stoichiometric amount is used, excess borane may be present after the reaction Which may cause other undesired reactions.

The reaction of the silane can be conducted with or without a solvent. The solvents which may be used herein include any which act as a solvent for the borane, the silane and the boron modified silane without adversely affecting any of the species. Examples of such solvents include alkanes such as pentane, hexane, heptane, octane etc, ethers such as tetrahydrofuran, or aromatic hydrocarbons such as benzene, toluene, xylene etc. Generally, if the borane-tetrahydrofuran complex is used in the reaction it is convenient to use tetrahydrofuran or mixtures with aromatic hydrocarbons as the solvent.

The reaction of the silane and borane is conducted by mixing the silane and the borane in a suitable reaction vessel. This reaction can be performed at any suitable temperature or pressure and in any convenient atmosphere. For simplicity, however, it is generally run at room temperature under an inert atmosphere and at atmospheric pressure. Since an exotherm generally occurs when the silane and the borane are mixed, it is often preferred to control the exotherm by slowly adding the borane to a solution of the silane. Continued stirring of this mixture (e.g., for 1-24 hours) results in formation of the desired modified silane.

The boron modified silane produced by the above reaction is then merely recovered from solution. Numerous methods such as simple evaporation or stripping of the solvent under heat and/or vacuum are known in the art and useful herein.

Although one specific crosslinker is detailed above, other boron modified silazanes would also function herein. For instance, boron modified hexamethyldisilazane and materials of the structure $R_3SiNBH_2SiR_2NBH_2SiR_3$ are useful herein, Such other crosslinkers are either known in the art or can be prepared using methods known in the art.

The above crosslinkers are then mixed with the polysilazane and the crosslinking reaction is initiated.

The polysilazane and the crosslinker may be mixed together in their liquid state or, alternatively, they may be blended in a solvent. The solvents which may be used herein include any which act as a solvent for both the polysilazane and the crosslinker and which do not cause rearrangement of either species. Examples of such solvents include alkanes such as pentane, hexane, heptane, octane etc., ethers such as tetrahydrofuran, or aromatic hydrocarbons such as benzene, toluene, xylene etc.

The crosslinker and the polysilazane may be blended in nearly any ratio desired to provide sufficient tack, flow, and final cure. Generally, however, the crosslinker is present in an amount of at least about 0.01 wt. % crosslinker based on the weight of the polysilazane with a range of about 0.01 to about 50 wt. % being preferred. In addition, it is also contemplated herein that several polysilazanes (e.g., of varying viscosity), several crosslinkers or other desirable materials (e.g., ceramic fillers) may be blended with the mixture to provide desirable properties.

The polysilazane/crosslinker mixture is then exposed to conditions which facilitate the crosslinking reaction. Generally, this involves merely heating the mixture to a sufficient temperature. Temperatures in the range of 50°–500° C., are generally sufficient. Other means of inducing crosslinking such as radiation or crosslinking catalysts are, however, also contemplated.

The polysilazane and crosslinker blend is useful for many purposes such as in the formation of fibers, monoliths and as matrices for ceramic matrix composites. In addition, the material may be used to impregnate porous ceramic bodies to increase density.

The following non-limiting examples are provided so that one skilled in the art may more fully understand the invention. In these examples, $^1$H NMR spectra were recorded on a Varian or EM390 spectrometer. FTIR data were recorded on a Perkin Elmer Series 1600 spectrometer. Gel permeation chromatography (GPC) data were obtained on a Waters GPC equipped with a model 600 E systems controller, a model 490 UV and model 410 Differential Refractometer detectors: all values are relative to polystyrene. TMA data were recorded on a Du Pont 940 thermomechanical analyzer (TMA) interfaced to an Omnitherm 2066 computer.

Carbon, hydrogen and nitrogen analyses were performed on a Control Equipment Corporation 240-XA Elemental Analyzer. Boron and silicon was determined by a fusion technique which consisted of converting the silicon material to soluble forms of silicon and analyzing the solute for total silicon by atomic absorption spectrometry.

All furnace firings were done in an Astro graphite furnace equipped with Eurotherm temperature controllers. The furnace was equipped with an Ircon Modeline Plus optical pyrometer to monitor the temperature above 900° C.

EXAMPLE 1: Preparation of Boron Modified Tris(trimethylsilylamino)silane

Route A

A 500 mL 3 necked flask fitted with an argon inlet, an overhead stirrer and an addition funnel was charged with 29.3 g tris(trimethylsilylamino)silane (0.10 mole) distilled from the reaction of trichlorosilane and hexamethyldisilazane under argon. The addition funnel was charged with 300 mL of a 1.0M BH$_3$-THF solution in THF (obtained from Aldrich Chemical Company). This borane solution was added to the flask over a 2 hour period which was accompanied by a mild exotherm and gas evolution. The resulting solution was stirred 16 hours and then stripped of volatiles at 60° C. in vacuo resulting in 32 g of a liquid product.

The IR spectrum of tris(trimethylsilylamino)silane was compared with the above boron modified product. The spectrum of the boron modified product showed stretches at 2450 cm$^{-1}$ and 1350 cm$^{-1}$ indicating the presence of B—H and N—H bonds respectively. Additionally, stretches at 3350 cm$^{-1}$ indicating the presence of N—H bonds were decreased in the boron modified product.

Route B

A 1 L 3 necked flask fitted with an argon inlet, an overhead stirrer and an addition funnel was charged with 500 mL of a 1.0M BH$_3$-THF solution in THF (obtained from Aldrich Chemical Company). The addition funnel was charged with 54 g tris(trimethylsilylamino)silane (0.18 mole) distilled from the by-products of the reaction of trichlorosilane and hexamethyldisilazane under argon. The silane was added to the flask over a 1 hour period which was accompanied by a mild exotherm and gas evolution. The resulting solution was stirred 48 hours and then stripped of volatiles at 60° C, in vacuo resulting in 57 g of a liquid product.

EXAMPLE 2: Cure Properties

Hydridopolysilazane made by the method of Cannady in U.S. Pat. No. 4,540,803 was blended with the boron modified tris(trimethylsilylamino)silane of Example 1 at 30 parts per weight crosslinker per 100 parts hydridopolysilazane in a toluene solution. As a control, tris(trimethylsilylamino)silane was also blended with the hydridopolysilazane in the same amounts. These solutions were then used to impregnate fiber braids suitable for torsional braid analysis (TBA). The braids were dried, placed in a TBA spectrometer for testing and heated to 288° C, for 6 hours. The storage modulus is equivalent to the stiffness of the sample and shows that the sample containing the boron modified crosslinker increases in stiffness corresponding to the crosslinking reaction. The fact that little increase in stiffness is seen with the control implies that very little crosslinking is occurring in that system

EXAMPLE 3: Char Composition

Hydridopolysilazane made by the method of Cannady in U.S. Pat. No. 4,540,803 (Mw=10,000) was blended with the boron modified tris(trimethylsilylamino)silane of Example 1 at varying ratios. The blends were fired at 1400° C., to determine the effect of the crosslinker on the composition of the final ceramic. The results are presented in the following table. It should be noted that the crosslinker does not have a significant impact on the final ceramic char, especially the carbon content which could be detrimental to the composite oxidation properties.

| Parts Crosslinker/ 100 parts HPZ | Char Yield | % C | % N |
| --- | --- | --- | --- |
| — | 69.60 | 11.82 | 28.17 |
| 10 | 70.08 | 12.40 | 26.54 |
| 20 | 70.19 | 12.49 | 25.76 |
| 30 | 71.11 | 12.32 | 24.60 |

That which is claimed is:

1. A silazane crosslinker of the structure:

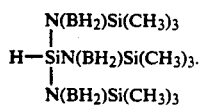

2. A method of forming a crosslinker of the structure:

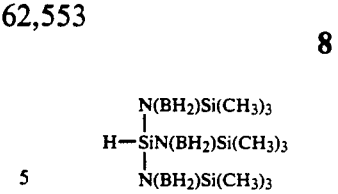

comprising reacting tris(trimethylsilylamino)silane with borane for a time and a temperature sufficient to form the crosslinker.

3. The method of claim 2 wherein the amount of borane is about three moles of borane per mole of tris(trimethylsilylamino)silane.

4. The method of claim 2 wherein the reaction is run at room temperature under an inert atmosphere and at atmospheric pressure.

5. The method of claim 2 wherein the reaction is conducted in a solvent.

* * * * *